US00PP19405P2

(12) United States Plant Patent
Brown

(10) Patent No.: US PP19,405 P2
(45) Date of Patent: Nov. 4, 2008

(54) ***DIASCIA* PLANT NAMED 'CODI110'**

(50) Latin Name: *Diascia×hybrida*
Varietal Denomination: Codi110

(75) Inventor: Graham Noel Brown, Pennant Hills (AU)

(73) Assignee: Nuflora International Pty. Ltd., Macquarie Fields, New South Wales (AU)

( * ) Notice: Subject to any disclaimer, the term of this patent is extended or adjusted under 35 U.S.C. 154(b) by 188 days.

(21) Appl. No.: 11/527,869

(22) Filed: Sep. 27, 2006

(51) Int. Cl.
*A01H 5/00* (2006.01)

(52) U.S. Cl. ..... Plt./425

(58) Field of Classification Search ..... Plt./425
See application file for complete search history.

*Primary Examiner*—Anne Marie Grunberg
*Assistant Examiner*—Georgia Helmer
(74) *Attorney, Agent, or Firm*—C. A. Whealy

(57) ABSTRACT

A new and distinct cultivar of *Diascia* plant named 'Codi110', characterized by its compact, upright and somewhat outwardly spreading plant habit; freely flowering habit; and dark red purple-colored flowers.

1 Drawing Sheet

Botanical designation: *Diascia×hybrida.*
Cultivar denomination: 'CODI110'.

BACKGROUND OF THE INVENTION

The present invention relates to a new and distinct cultivar of *Diascia,* botanically known as *Diascia×hybrida,* and hereinafter referred to by the name 'Codi110'.

The new *Diascia* is a product of a planned breeding program conducted by the Inventor in Cobbitty, New South Wales, Australia. The objective of the breeding program is to create new freely-flowering *Diascia* cultivars with uniform plant habit and attractive flower colors.

The new *Diascia* originated from a cross-pollination made by the Inventor in Cobbitty, New South Wales, Australia in September, 2001 of a proprietary selection of *Diascia×hybrida* identified as code number X99.54.7, not patented, as the female, or seed, parent with a proprietary selection of *Diascia×hybrida* identified as code number X99.54.1, not patented, as the male, or pollen, parent. The cultivar Codi110 was discovered and selected by the Inventor as a flowering plant within the progeny of the stated cross-pollination in a controlled environment in Cobbitty, New South Wales, Australia in October, 2002.

Asexual reproduction of the new *Diascia* by terminal cuttings in a controlled environment in Macquarie Fields, New South Wales, Australia since 2002, has shown that the unique features of this new *Diascia* are stable and reproduced true to type in successive generations.

SUMMARY OF THE INVENTION

The cultivar Codi110 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Codi110'. These characteristics in combination distinguish 'Codi110' as a new and distinct cultivar of *Diascia:*

1. Compact, upright and somewhat outwardly spreading plant habit.
2. Freely flowering habit.
3. Dark red purple-colored flowers.

Plants of the new *Diascia* can be compared to plants of the female parent selection. Plants of the new *Diascia* differ from plants of the female parent selection in the following characteristics:

1. Plants of the new *Diascia* are more outwardly spreading than plants of the female parent selection.
2. Plants of the new *Diascia* have larger flowers than plants of the female parent selection.

Plants of the new *Diascia* can be compared to plants of the male parent selection. Plants of the new *Diascia* differ primarily from plants of the male parent selection in flower color as plants of the new *Diascia* have darker-colored flowers.

Plants of the new *Diascia* can be compared to plants of the *Diascia×hybrida* cultivar Red Ace, disclosed in U.S. Plant patent application Ser. No. 09/639,898. In side-by-side comparisons conducted in Macquarie Fields, New South Wales, Australia, plants of the new *Diascia* differed from plants of the cultivar Red Ace in the following characteristics:

1. Plants of the new *Diascia* were more compact than plants of the cultivar Red Ace.
2. Plants of the new *Diascia* had larger flowers than plants of the cultivar Red Ace.
3. Flowers of plants of the new *Diascia* and the cultivar Red Ace differed in flower color as plants of the cultivar Red Ace had red-colored flowers.

BRIEF DESCRIPTION OF THE PHOTOGRAPHS

The accompanying colored photographs illustrate the overall appearance of the new *Diascia,* showing the colors as true as it is reasonably possible to obtain in colored reproductions of this type. Colors in the photographs may differ slightly from the color values cited in the detailed botanical description which accurately describe the colors of the new *Diascia.*

The photograph at the bottom of the sheet comprises a side perspective view of a typical flowering plant of 'Codi110' grown in a container.

The photograph at the top of the sheet comprises a close-up view of typical flowers of 'Codi110'.

DETAILED BOTANICAL DESCRIPTION

The photographs and following observations, measurements and values describe plants grown in Encinitas, Calif. in 12.5-cm containers in polyethylene-covered greenhouses during the spring and under conditions which closely approximate commercial production. During the production of the plants, day temperatures averaged 24° C., night temperatures averaged 19° C. and light levels averaged 4,000 foot-candles. Plants were pinched twice and were about 14 weeks old when the photographs and the description were taken. In the description, color references are made to The Royal Horticultural Society Colour Chart, 1995 Edition, except where general terms of ordinary dictionary significance are used.

Botanical classification: *Diascia×hybrida* cultivar Codi110.

Parentage:

*Female, or seed, parent.*—Proprietary selection of *Diascia×hybrida* identified as code number X99.54.7, not patented.

*Male or pollen parent.*—Proprietary selection of *Diascia×hybrida* identified as code number X99.54.1, not patented.

Propagation:

*Type.*—By terminal vegetative cuttings.

*Time to initiate roots, summer and winter.*—About one week at temperatures of 20° C.

*Time to develop roots, summer and winter.*—About three weeks at temperatures of 20° C.

*Root description.*—Fine, fibrous; white in color.

*Rooting habit.*—Freely branching; dense.

Plant description:

*Plant form and growth habit.*—Compact, upright and somewhat outwardly spreading plant habit. Vigorous growth habit.

*Branching habit.*—Freely branching, usually about ten primary lateral branches each with potentially two secondary lateral branches per node.

*Plant height.*—About 24 cm.

*Plant diameter (area of spread).*—About 32 cm.

Lateral branch description:

*Length.*—About 21 cm.

*Diameter.*—About 1.5 mm.

*Internode length.*—About 4 mm.

*Texture.*—Smooth, glabrous.

*Color.*—144A.

Foliage description:

*Arrangement.*—Opposite, simple.

*Length.*—About 2.4 cm.

*Width.*—About 1.5 cm.

*Shape.*—Elliptical with cordate tendencies.

*Apex.*—Broadly acute to rounded.

*Base.*—Cordate.

*Margin.*—Shallow and irregular serrated.

*Texture, upper and lower surfaces.*—Smooth, glabrous.

*Venation pattern.*—Palmate; arcuate.

*Color.*—Developing foliage, upper surface: 147B. Developing foliage, lower surface: 147C. Fully developed foliage, upper surface: 146A; venation, 146B. Fully developed foliage, lower surface: 147C; venation, 147C.

*Petiole.*—Length: About 3 mm. Diameter: About 1.5 mm. Texture, upper and lower surfaces: Smooth, glabrous. Color, upper surface: 146A. Color, lower surface: 146C.

Flower description:

*Flower arrangement.*—Single flowers arranged on loose terminal racemes. Freely flowering habit with usually about 24 open flowers and flower buds per lateral branch. Flowers face upright and outwardly. Flowers not fragrant.

*Natural flowering season.*—Plants flower continuously throughout the spring in southern California. Flowers last about five days on the plant. Flowers not persistent.

*Inflorescence height.*—About 10.8 cm.

*Inflorescence width.*—About 4.5 cm.

*Flower diameter.*—About 1.7 cm.

*Flower length (height).*—About 9 mm.

*Flower bud.*—Length: About 6 mm. Diameter: About 7 mm. Shape: Rounded. Color: 70A.

*Petals.*—Arrangement: Corolla consists of five petals modified into two banner petals, two lateral petals with spurs and a protruding lip petal. Length: Banner petals: About 8 mm. Lateral petals (including spurs): About 7 mm. Lower lip petal: About 1 cm. Width: Banner petals: About 5 mm. Lateral petals: About 6 mm. Lower lip petal: About 1.1 cm. Shape: Rounded. Apex: Rounded. Base: Attenuate. Margin: Entire. Texture, upper and lower surfaces: Smooth, glabrous, satiny. Color: When opening, upper surface: 63A. When opening, lower surface: 70A. Fully opened, upper surface: 60A; towards the base, 61A; central eyespot, 11A. Fully opened, lower surface: 60C; nectar spurs, 59A.

*Sepals.*—Appearance: Five sepals fused into a star-shaped calyx. Length: About 3 mm. Width: About 1 mm. Shape: Elliptical. Apex: Acute. Margin: Entire. Texture, upper surface: Smooth, glabrous. Texture, lower surface: Minute pubescence. Color, upper and lower surfaces: 146B.

*Peduncles.*—Length: About 4.5 cm. Diameter: About 1 mm. Angle: Erect to about 45° from vertical. Strength: Strong. Texture: Scattered pubescence. Color: 146A.

*Pedicels.*—Length: About 1.8 cm. Diameter: Less than 1 mm. Angle: About 45° from vertical. Strength: Moderately strong. Texture: Scattered pubescence. Color: 146A.

*Reproductive organs.*—Androecium: Stamen number: About four. Anther shape: Ovoid. Anther length: Less than 1 mm. Anther color: 10A. Amount of pollen: Scarce. Pollen color: 12A. Gynoecium: Pistil length: About 4 mm. Style length: About 2 mm. Style color: 146C. Stigma appearance: Rounded. Stigma color: 144B. Ovary color: 146C.

*Seed/fruit.*—Seed and fruit production has not been observed.

Temperature tolerance: Plants of the new *Diascia* have been observed to tolerate temperatures from about 2° C. to about 29° C.

Pathogen/pest resistance: Plants of the new *Diascia* have not been shown to be resistant to pathogens and pests common to *Diascia*.

It is claimed:

1. A new and distinct *Diascia* plant named 'Codi110' as illustrated and described.

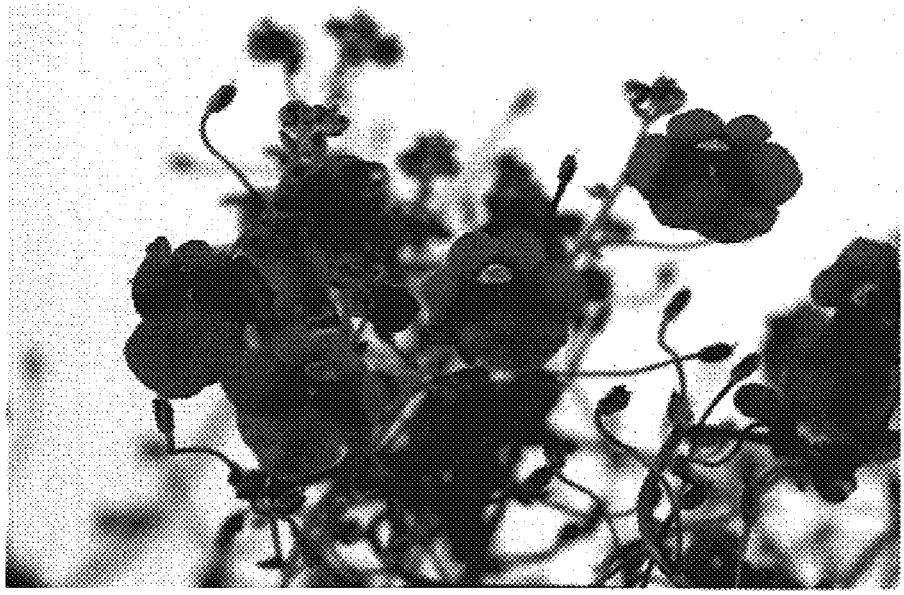
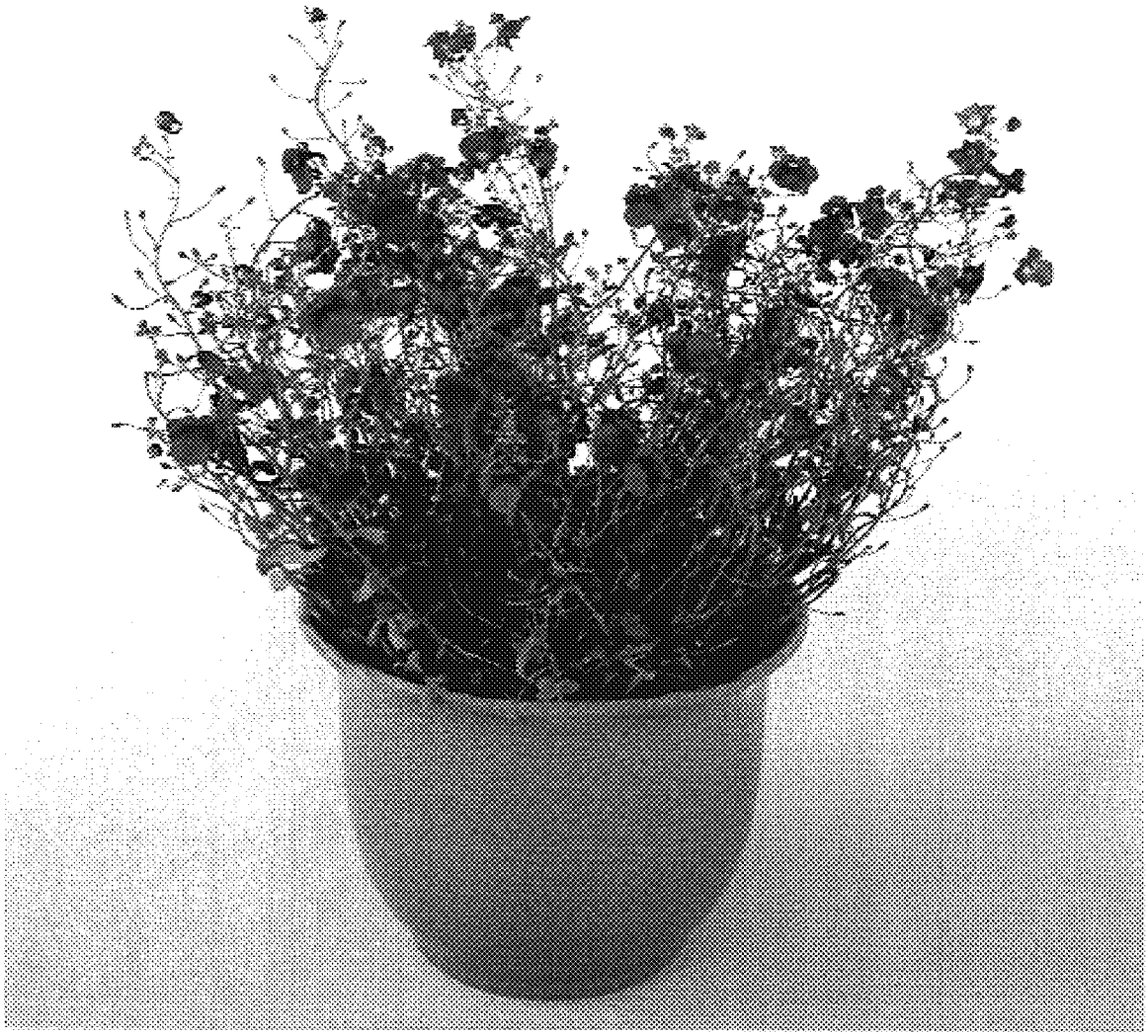

* * * * *